United States Patent [19]

Baker

[11] Patent Number: 4,874,843

[45] Date of Patent: Oct. 17, 1989

[54] CHROMATOGRAPHIC PURIFICATION PROCESS

[75] Inventor: Patrick J. Baker, Greenwood, Ind.

[73] Assignee: Eli Lilly and Company, Indianapolis, Ind.

[21] Appl. No.: 128,351

[22] Filed: Dec. 3, 1987

[51] Int. Cl.$^4$ .............................................. C07K 1/14
[52] U.S. Cl. ..................................... 530/317; 530/322; 530/344
[58] Field of Search ...................... 530/317, 322, 344

[56] References Cited

U.S. PATENT DOCUMENTS

| | | | |
|---|---|---|---|
| 3,515,717 | 6/1970 | Cha et al. | 260/210 |
| 4,208,403 | 6/1980 | Hamill et al. | 424/115 |
| 4,440,753 | 4/1984 | McCormick et al. | 424/124 |
| 4,537,717 | 8/1985 | Abbott et al. | 260/112.5 |
| 4,719,287 | 1/1988 | Login et al. | 530/317 |

FOREIGN PATENT DOCUMENTS 0145484 11/1984 European Pat. Off. .

OTHER PUBLICATIONS

Leaflet "Isolation of Antibiotics from Fermentation Broths by DIAION HP 20, A Synthetic Adsorbent", Mitsubishi Chemical Industries Limited, pp. 1-22.
Grieser et al., "Liquid Chromatography on a Porous Polystyrene—Divinylbenzene Support", Analytical Chemistry, vol. 45, No. 8, Jul. 1973, pp. 1348-1353.

*Primary Examiner*—Lester L. Lee
*Attorney, Agent, or Firm*—Mary Ann Tucker; Leroy Whitaker

[57] ABSTRACT

This invention relates to a new chromatographic process for purifying fermentation products, particularly the antibiotic LY146032, from fermentation broths by use of a reverse phase non-functional resin.

In the process of this invention the resin is loaded with the compound in the aqueous phase, the water then is removed from the resin and the resin converted to the organic phase for the resolution step. This process is applicable to purifying compounds which are adsorbed on reverse phase non-functional resins.

11 Claims, No Drawings

CHROMATOGRAPHIC PURIFICATION PROCESS

SUMMARY OF THE INVENTION

This invention relates to a new chromatographic process for purifying fermentation products, particularly the antibiotic LY146032, from fermentation broths by use of a non-functional resin in reverse mode.

In the process of this invention the resin is loaded with the compound in the aqueous phase, the water then is physically removed from the resin and the resin rewetted with a polar organic solvent for the resolution step. This process is applicable to purifying compounds which are adsorbed on non-functional resins.

BACKGROUND OF THE INVENTION

The antibiotic LY146032 is the N-decanoyl derivative of the A-21978C antibiotics and has now been identified as a member of factor A-21978C$_0$. The A-21978C antibiotics are prepared by fermentation methods described in U.S. Pat. No. 4,208,403. LY146032 methods for its preparation are specifically disclosed in U.S. Pat. No. 4,537,717. In this method A-21978C is prepared by fermentation techniques. The fatty acid side chain then is removed with an enzyme to give the A-21978C nucleus and the nucleus is reacylated with the desired acyl group, for example the n-decanoyl group, to give the A-21978C cyclic peptides as described in U.S. Pat. No. 4,527,717.

An improved method for preparing these cyclic peptides is described by Floyd M. Huber, Richard L. Pieper and Anthony J. Tietz in copending U.S. patent application Ser. No. 773,762, filed Sept. 9, 1985, entitled IMPROVED PROCESS FOR A-21978C DERIVATIVES.

Because of the interest in LY146032 and other therapeutically useful fermentation products and their importance, new and more effective methods of isolating these useful compounds from fermentation mixtures continually are sought.

The novel process of this invention was previously disclosed, but not claimed, in U.S. patent application No. 07/060,148, filed June 10, 1987, for use in purifying the β-isomer of LY146032.

DETAILED DESCRIPTION

The present process provides a novel method for the separation and purification of a wide variety of fermentation products, including the antibiotic LY146032, from their fermentation broths or partially purified process streams by adsorbing the antibiotic from aqueous medium onto a non-functional resin, followed by physically removing the water from the resin, rewetting the resin with a polar organic solvent and eluting the product by increasing the polarity of the solvent.

Prior to the present invention, the partial purification of LY146032 was accomplished by filtering the whole fermentation broth and passing the filtrate through a column containing HP-20 resin (Diaion High Polymer HP-Series, Mitsubishi Chemical Industries Limited, Tokyo, Japan). The column is washed with water and water:acetonitrile (about 90:10 to about 80:20), and the LY146032 eluted with water:aceonitrile (about 60:40). Elution is monitored by paper chromatography or ultraviolet monitor and fractions containing LY146032 are collected, concentrated under vacuum freeze-dried.

This procedure gives semi-pure LY146032 which then is dissolved in an acetonitrile-methanol-sodium acetate buffer solvent and passed through a column containing HP-20ss non-fumnctional macroreticular resin. The column is developed with the same solvent and the purified fractions containing LY146032 are combined, diluted with water and loaded on a column containing HP-20 resin. The column is washed with water to remove salts, eluted with acetonitrile:water (about 60:40) and the LY146032 fractions collected. These steps must be repeated as often as necessary to give a product of the desired purity.

Final resolution and separation of LY146032 from structurally similar compounds is impeded by the presence of impurities which are not identifiable by ultraviolet analysis of the fermentation broth. These so-called "non-uv" impurities are primarly saponins and other fragments. These compounds have solubility characteristics similar to LY146032 and are difficult to separate from LY146032. The presence of these compounds causes foaming during concentration procedures and poor resolution during subsequent chromatographic sepration steps.

Attempts to remove these impurities by various chromatographic methods, including reverse-phase chromatography on silica gel/C18 (Quantum LP-1), normal phase chromatography over silica gel, and ion-exchange chromatography, failed to significantly improve the purity of LY146032 over the use of HP-20 as described above. All of these methods are plagued by low capacity, poor resolution and low recovery of LY146032.

A novel isolation procedure had to be developed to overcome these problems. Thus, it was unexpectedly found that replacing the first HP-20 step described above with a "reverse method" procedure, wherein adsorption is carried out with the non-functional resin in aqueous phase (polar) and resolution is carried out with the resin in organic phase (non-polar), achieves substantial improvements in both purity and yield of the product. The "reverse method" process of this invention improves the purity of LY146032 twofold and, since it removes impurities that interfere with the subsequent purification steps, improves the final purity from about 80% to about 93%. In addition, the overall yield is increased from about 5% to about 35%.

An additional benefit of the "reverse method" process is that fewer subsequent separation steps are required to achieve the increased purity and yield. LY146032 is susceptible to transpeptidation degradation (U.S. patent application No. 07/060,148, filed June 10, 1987). Reducing the number of steps and the time required to purify the product greatly lessens the formation of transpeptidation by-products.

The novel process of the present invention is useful for purifying fermentation products that are adsorbed onto non-functional resins. These fermentation products include lipopeptides, for example LY146032, echinocandin B and the like, and glycopeptides, for example vancomycin, actoplanin, teichoplanin, A82846 and the like.

The present invention begins with clarified, acidic aqueous broth containing the fermentation product or with partially purified fermentation product in an acidic aqueous buffer solution. The process comprises:

a. contacting an aqueous solution of a fermentation product with a non-functional resin in aqueous phase;

b. physically removing the water from the charged resin;

c. rewetting the charged resin with a polar organic solvent;

d. washing the resin with a polar organic solvent to remove non-uv impurities;

e. eluting the fermentation product from the non-functional resin by increasing the polarity of the solvent; and f. recovering the ferementation product.

When the process begins with whole broth, the broth is filtered and the pH adjusted to about pH 4.0 to about pH 5.0, preferably about pH 4.5, using aqueous acetic, hydrochloric sulfuric, phosphoric and like acids.

When the process begins with partially purified fermentation product, the product is dissolved in an aqueous buffer solution of about pH 40 to about pH 5.0, preferably about pH 4.5. Suitable buffer solutions are aqueous solutions of sodium phosphate, ammonium phosphate, ammonium acetate, sodium acetate and the like. Preferably, the buffer is sodium acetate.

The fermentation product containing solution is passed over a column containing the non-functional resin in aqueous phase. Non-functional resins useful in the process of this invention can be described generally as macroporous copolymers of styrene and divinylbenzene. Non-functional resins are a known class of resins and information concerning these resins, their sources and their characteristics appears in *J. Chromatography* 201, 287–292 (1980). Typical non-functional resins include Diaion HP-20, Doulite ES-861, Amberlite XAD-16, Amberlite XAD-4 and the like. Diaion HP-20 is a preferred non-functional resin.

The resin is removed from the column and filtered or dried to remove the water. The resin may be dried in a vacuum oven or air dried, for example in a Handy Dandy Filter (Sharples Filter Co.). The charged resin then is rewetted with a polar organic solvent. If the resin is substantially dry, rewetting may take place either by adding the resin to the polar organic solvent or by adding the polar organic solvent to the resin. If appreciable amounts of water remain in the resin, the resin must be added slowly to the polar organic solvent to avoid stripping the fermentation product from the resin. The resin then is repacked into a column and is washed with a polar organic solvent to remove non-uv impurities. The fermentation product is eluted from the resin by increasing the polarity of the solvent.

In the above process, the term "polar organic solvent" includes methanol, ethanol, acetone, n-propyl alcohol, isobutyl alcohol, n-butyl alcohol, methyl ethyl ketone, acetonitrile, tetrahydrofuran, and like solvents which have appreciable water solubility or are miscible with water. Acetonitrile is a preferred polar organic solvent. The polar organic solvent may be acidified with from about 1% to about 10% aqueous acid, preferably about 5% aqueous acid. Aqueous acetic, hydrochloric, sulfuric, phosphoric and like acids may be used. Acidification to about pH 4.0 to about pH 5.0 improves the resolution of the process and, when the fermentation product is LY146032, reduces the amount of transpeptidation by-product formed.

In the elution step, the polarity of the solvent is increased by diluting the polar organic solvent with a more polar solvent, for example water or methanol. For example, the fermentation product may be eluted with an acetonitrile:water solvent in the ratio of from about 95:5 to about 40:60, preferably from about 85:15 to about 80:20.

The fermentation product is recovered from the eluate by methods known in the art, for example crystallization, concentration and lyophilization.

The invention is illustrated by the following examples, which are not to be considered as limiting.

EXAMPLE 1

Purification of LY146032

Crude LY146032 (137.5 g) was dissolved in 3.5 l of 1% sodium acetate buffer at pH 4.5. The solution was passed through a column containing 3 l of HP-20 resin (Diaion High Porous Polymer HP-series, Mitsubishi Chemical Industries Limited, Tokyo, Japan). The effluent was discarded. The resin was washed with 30 l of chilled deionized water and the wash water was discarded.

The resin, charged with LY146032, was removed from the column and filtered to remove residual water. The charged, semi-dry resin then was added slowly to 32 l of acetonitrile. The charged resin in acetonitrile was repacked into the column.

The column was washed with 48 l of acetonitrile-water solution (95:5) to remove the non-uv impurities, e.g., the saponins and tripeptide fragments. The column was eluted with 17 l acetonitrile-water solution (85:15). One liter fractions were collected. The elution was monitored by analytical HPLC and fractions containing LY146032 were combined.

The LY146032 containing fractions were diluted with five volumes of chilled deionized water and passed through a column containing 500 ml of HP-20 resin. The column was washed with 500 ml deionized water to remove salts. The column was eluted with acetonitrile-water solution (60:40). Fractions shown by HPLC to contain LY146032 were combined, concentrated and lyophilized to provide 53.3 g (60% yield) of 89.3% purity LY146032.

EXAMPLE 2

Purification of LY146032

Crude concentrate (157 l) containing 1914.2 g of LY146032 activity (purity 24.4%) was diluted to 600 l with chilled purified water. HP-20 resin (60 l) was added to the diluted crude concentrate. The pH was adjusted to 4.7 with glacial acetic acid, n-butanol (6 l) was added to control foaming, and the mixture was stirred for 20 hours. The resin then was washed with 300 l of water.

The charged resin was put in a Handy Dandy Filter and blown dry. The dried, charged resin was rewetted with acetonitrile (600 l) and loaded into a column. The column was washed with acetonitrile (60 l).

The resin was washed with a mixture of acetonitrile:methanol:0.25% phosphoric acid (80:15:5) to remove non-uv impurities. The column was eluted with 120 l of acetonitrile:water solution (80:20). Fractions (25 l) were collected and the fractions containing LY146032 were combined. The combined fractions were concentrated and freeze-dried to provide 993.1 g (51.9% yield) of LY146032 (purity 50.5%).

EXAMPLE 3

Purification of Echinocandin B

Fermentation whole broth (200 L ml) containing 22.75 mg of Echinocandin B was diluted with two volumes (400 ml) of methanol. The insoluble mycelial solids were removed by filtration. The pH was adjusted to 5.0 with 5N hydrochloric acid and the filtrate was added to HP-20 resin (10 ml). The mixture was diluted with an equal volume of water and stirred for 60 minutes to effect adsorption of the Echinocandin B onto the resin. The charged resin was separated by filtration and dried for 16 hours at 25° C. in a vacuum oven. The dry, charged resin was rewetted with acetonitrile and packed into a column. The column was washed with three column volumes of acetonitrile. Elution with three column volumes of 90% acetonitrile/10% water resulted in recovery of 26% yield with a purity equivalent to the reference sample. Further elution with three column volumes of 80% acetonitrile/20% water resulted in the additional recovery of 38% yield with a purity of 41.2% of the reference sample.

I claim:

1. A process for purifying fermentation products which comprises:
   a. contacting an aqueous solution of a fermentation product with a non-functionalized macroporous copolymer of styrene and divinylbenzene in aqueous phase;
   b. physically removing the water from the charged resin;
   c. rewetting the charged resin with a polar organic solvent;
   d. washing the resin with a polar organic solvent that is the same as or different than the polar organic solvent used in step (C) to remove non-uv impurities;
   e. eluting the fermentation product from the non-functional resin by increasing the polarity of the solvent; and
   f. recovering the fermentation product.

2. The process of claim 1 wherein the fermentation product is a lipopeptide.

3. The process of claim 2 wherein the fermentation product is LY146032.

4. The process of claim 2 wherein the fermentation product is Echinocandin B.

5. The process of claim 1 wherein the fermentation product is a glycopeptide.

6. The process of claim 4 wherein the fermentation product is vancomycin.

7. The process of claim 1 wherein the resin is Diaion HP-20.

8. The process of claim 1 wherein the resin is amberlite XAD-4.

9. The process of claim 1 wherein the polar organic solvent is acetonitrile.

10. The process of claim 1 wherein the fermentation product is eluted from the non functionalized macroporous copolymer of styrene and divinylbenzene with acetonitrile containing from about 5% to about 60% water.

11. The process of claim 9 wherein the fermentation product is eluted from the non-functionalized macroporous copolymer of styrene and divinylbenzene with acetonitrile containing from about 10% to about 20% water.

* * * * *